(12) United States Patent
Viola

(10) Patent No.: US 8,758,404 B2
(45) Date of Patent: *Jun. 24, 2014

(54) SURGICAL FASTENERS COATED WITH WOUND TREATMENT MATERIALS

(71) Applicant: Covidien LP, Mansfield, MA (US)

(72) Inventor: Frank J. Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/857,452

(22) Filed: Apr. 5, 2013

(65) Prior Publication Data

US 2013/0226230 A1    Aug. 29, 2013

Related U.S. Application Data

(63) Continuation of application No. 13/329,581, filed on Dec. 19, 2011, now Pat. No. 8,435,263, which is a continuation of application No. 11/250,231, filed on Oct. 14, 2005, now Pat. No. 8,097,017.

(60) Provisional application No. 60/620,068, filed on Oct. 18, 2004.

(51) Int. Cl.
*A61B 17/08* (2006.01)

(52) U.S. Cl.
USPC ........................................ 606/219

(58) Field of Classification Search
USPC .......... 606/138, 151, 157, 219, 220, 221, 75; 227/19, 176.1, 175.1
See application file for complete search history.

(56) References Cited

U.S. PATENT DOCUMENTS

| | | |
|---|---|---|
| 4,275,813 A | 6/1981 | Noiles |
| 4,506,670 A | 3/1985 | Crossley |
| 4,534,352 A | 8/1985 | Korthoff |
| 4,655,222 A | 4/1987 | Florez et al. |
| 5,016,784 A | 5/1991 | Batson |
| 5,258,012 A | 11/1993 | Luscombe et al. |
| 5,324,307 A | 6/1994 | Jarrett et al. |
| 5,342,395 A | 8/1994 | Jarrett et al. |
| 5,392,979 A | 2/1995 | Green et al. |
| 5,465,896 A | 11/1995 | Allen et al. |
| 5,505,736 A | 4/1996 | Reimels et al. |
| 5,550,172 A | 8/1996 | Regula et al. |
| 5,620,289 A | 4/1997 | Curry |
| 5,854,382 A | 12/1998 | Loomis |

(Continued)

FOREIGN PATENT DOCUMENTS

| | | |
|---|---|---|
| WO | WO 92/13491 | 8/1992 |
| WO | WO 01/56533 | 8/2001 |

(Continued)

OTHER PUBLICATIONS

International Search Report corresponding to PCT/US05/37264, completed Aug. 4, 2006 and mailed Sep. 19, 2006; (6 pp).

(Continued)

*Primary Examiner* — Gregory Anderson

(57) ABSTRACT

The present disclosure relates to surgical fasteners and more particularly to surgical fasteners coated with wound treatment materials. According to an aspect of the present disclosure, a surgical fastener for use in combination with a surgical fastener applying apparatus is provided. The surgical fastener includes a pair of legs; a crown interconnecting the pair of legs; and a wound treatment material coating at least a portion of the legs and crown.

8 Claims, 3 Drawing Sheets

(56) References Cited

U.S. PATENT DOCUMENTS

| | | |
|---|---|---|
| 6,296,607 B1 | 10/2001 | Milbocker |
| 6,325,805 B1 | 12/2001 | Ogilvie et al. |
| 6,330,965 B1 | 12/2001 | Milliman et al. |
| 6,408,489 B1 | 6/2002 | Cluggish |
| 6,524,343 B2 | 2/2003 | Storer et al. |
| 6,565,840 B1 | 5/2003 | Clark et al. |
| 6,566,406 B1 | 5/2003 | Pathak et al. |
| 6,620,846 B1 | 9/2003 | Jonn et al. |
| 6,656,193 B2 | 12/2003 | Grant et al. |
| 6,689,153 B1 | 2/2004 | Skiba |
| 6,702,731 B2 | 3/2004 | Milbocker |
| 6,817,508 B1 | 11/2004 | Racenet et al. |
| 6,894,140 B2 | 5/2005 | Roby |
| 7,128,748 B2 | 10/2006 | Mooradian et al. |
| 7,129,300 B2 | 10/2006 | Roby |
| 7,431,730 B2 | 10/2008 | Viola |
| 7,527,632 B2 | 5/2009 | Houghton et al. |
| 8,016,881 B2 | 9/2011 | Furst |
| 8,097,017 B2 | 1/2012 | Viola |
| 2004/0044364 A1 | 3/2004 | DeVries et al. |
| 2004/0068078 A1 | 4/2004 | Milbocker |
| 2004/0093024 A1 | 5/2004 | Lousararian et al. |
| 2004/0167572 A1 | 8/2004 | Roth et al. |
| 2005/0113936 A1 | 5/2005 | Brustad et al. |
| 2005/0136090 A1 | 6/2005 | Falotico et al. |

FOREIGN PATENT DOCUMENTS

| | | |
|---|---|---|
| WO | WO 02/44278 | 6/2002 |
| WO | WO 03/071962 | 9/2003 |
| WO | WO 03/094746 | 11/2003 |
| WO | WO 2004/105821 | 12/2004 |

OTHER PUBLICATIONS

Extended European Search Report corresponding to EP 05 81 0430.8, completed Jan. 18, 2012 and mailed Jan. 25, 2012; (3 pp).

SURGICAL FASTENERS COATED WITH WOUND TREATMENT MATERIALS

CROSS-REFERENCE TO RELATED APPLICATIONS

This application is a continuation of U.S. application Ser. No. 13/329,581 filed Dec. 19, 2011, which is a continuation of U.S. application Ser. No. 11/250,231 filed Oct. 14, 2005 (U.S. Pat. No. 8,097,017) which claims benefit of application No. 60/620,068 filed Oct. 18, 2004, and the disclosures of each of the above-identified applications are hereby incorporated by reference in their entirety.

BACKGROUND

1. Technical Field

The present disclosure relates to surgical fasteners and more particularly to surgical fasteners coated with wound treatment materials.

2. Description of Related Art

Generally, coatings for medical devices are useful to create a water absorbent and lubricious coating for surgical instruments, for in-dwelling biomaterials such as stents, screws and internal splints, and for tubing, catheters, wire guides, and the like. Such coatings minimize the trauma of contact of the medical device with tissues and biological fluids. In particular, coatings have been used to provide a slippery and lubricious coating for reducing the coefficient of friction of a surface of a medical device to facilitate movement and maneuverability of the device. Lubricious coatings made from hydrophilic polymers are well-known in the art.

Medical devices such as surgical fasteners and staples have replaced suturing when joining or anastomosing various body structures, such as, for example, the bowel or bronchus. The surgical stapling devices employed to apply these staples are generally designed to simultaneously cut and seal an extended segment of tissue in a patient, thus vastly reducing the time and risks of such procedures.

Linear or annular surgical stapling devices are employed by surgeons to sequentially or simultaneously apply one or more linear rows of surgical fasteners, e.g., staples or two-part fasteners, to body tissue for the purpose of joining segments of body tissue together and/or for the creation of anastomosis. Linear surgical stapling devices generally include a pair of jaws or finger-like structures between which body tissue to be joined is placed. When the surgical stapling device is actuated and/or "fired," firing bars move longitudinally and contact staple drive members in one of the jaws, and surgical staples are pushed through the body tissue and into/against an anvil in the opposite jaw thereby crimping the staples closed. A knife blade may be provided to cut between the rows/lines of staples. Examples of such linear surgical stapling devices are Models "GIA™", "Endo GIA™" and "Premium Multi-fire TA™" instruments available from United States Surgical, a Division of Tyco Health-Care Group, LP, Norwalk, Conn. and disclosed in, inter alia, U.S. Pat. No. 5,465,896 to Allen et al., U.S. Pat. No. 6,330,965 to Milliman et al., and U.S. Pat. No. 6,817,508 to Racenet et al., the entire contents of each of which are incorporated herein by reference.

Annular surgical stapling devices generally include an annular staple cartridge assembly including a plurality of annular rows of staples, typically two, an anvil assembly operatively associated with the annular cartridge assembly, and an annular blade disposed internal of the rows of staples.

Another type of surgical stapler is an end-to-end anastomosis stapler. An example of such a device is a Model "EEA™" instrument available from United States Surgical, a Division of Tyco Health-Care Group, LP, Norwalk, Conn. and disclosed in, inter alia, U.S. Pat. No. 5,392,979 to Green et al., the entire contents of which is incorporated herein by reference. In general, an end-to-end anastomosis stapler typically places an array of staples into the approximated sections of a patient's bowels or other tubular organs. The resulting anastomosis contains an inverted section of bowel which contains numerous "B" shaped staples to maintain a secure connection between the approximated sections of bowel.

In addition to the use of surgical staples, sealants, e.g., biological sealants, can be applied to the surgical site to guard against leakage. Typically, the biological sealants are manually applied to the outer surface of the staple line by a physician by spraying on, brushing on, swabbing on, or any combinations thereof. This manual application of biological sealant can lead to non-uniformity of the thickness of sealant across the staple line and/or omitting a portion of the intended coverage area due to inability to see or reach the desired location.

A need exists for surgical fasteners and the like for delivering wound treatment material to a target surgical site without adding additional steps or complications to the surgical procedure.

SUMMARY

The present disclosure relates to surgical fasteners and more particularly to surgical fasteners coated with wound treatment materials.

According to an aspect of the present disclosure, a surgical fastener for use in combination with a surgical fastener applying apparatus is provided. The surgical fastener includes a pair of legs; a crown interconnecting the pair of legs; and a wound treatment material coating at least a portion of the legs and/or crown.

The wound treatment material may be at least one of an adhesive, a sealant, a hemostat, and a medicament. In an embodiment, the surgical fastener is a staple. In another embodiment, the surgical fastener is a two-part fastener.

The legs and crown of the surgical fastener may be fabricated from at least one of a non-absorbable and a bio-absorbable material. It is envisioned that the non-absorbable material is at least one of stainless steel and titanium. The bio-absorbable material may be at least one of a homopolymers, copolymers, and a blend of monomers selected from the group consisting of glycolide, glycolic acid, lactide, lactic acid, p-dioxanone, α-caprolactone and trimethylene carbonate. The bio-absorbable material may also be at least one of Polyglycolic Acid (PGA) and Polylactic Acid (PLA).

The wound treatment material may be a sealant selected from the group consisting of acrylate, methacrylate functional hydrogels in the presence of a biocompatible photoinitiator, alkyl-cyanoacrylates, isocyanate functional macromers with or without amine functional macromers, succinimidyl ester functional macromers with amine or sulfhydryl functional macromers, epoxy functional macromers with amine functional macromers, mixtures of proteins or polypeptides in the presence of aldehyde crosslinkers, Genipin, water-soluble carbodiimides, and anionic polysaccharides in the presence of polyvalent cations.

The wound treatment material may also be a sealant selected from the group consisting of isocyanate terminated hydrophilic urethane prepolymers derived from organic polyisocyanates and oxyethylene-based diols or polyols; alpha-cyanoacrylate based adhesives; alkyl ester based cyanoacrylate adhesives; adhesives based on biocompatible cross-linked polymers formed from water soluble precursors having electrophilic and nucleophilic groups capable of reacting and cross-linking in situ; two part adhesive systems including those based upon polyalkylene oxide backbones substituted with one or more isocyanate groups in combination with bioabsorbable diamine compounds, or polyalkylene oxide backbones substituted with one or more amine groups in combination with bioabsorbable diisoycanate compounds; and isocyanate terminated hydrophilic urethane prepolymers derived from aromatic diisocyanates and polyols.

It is envisioned that the wound treatment material is a hemostat selected from the group consisting of fibrin-based, collagen-based, oxidized regenerated cellulose-based and gelatin-based topical hemostats.

It is contemplated that the wound treatment material is a medicament selected from the group consisting of drugs, enzymes, growth factors, peptides, proteins, pigments, dyes, diagnostic agents or hemostasis agents, monoclonal antibodies, or any other pharmaceutical used in the prevention of stenosis.

In an embodiment, the wound treatment material may be impregnated into the legs and the crown. In another embodiment, the wound treatment material completely coats the legs and the crown.

It is envisioned that each leg includes a sharpened distal end. It is further envisioned that the crown is linear or non-linear.

DETAILED DESCRIPTION OF THE EMBODIMENTS

Figure 1:
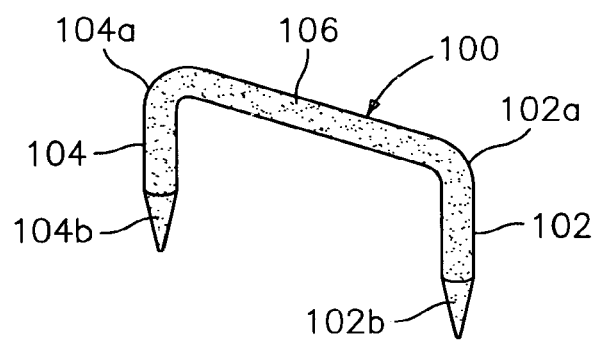
FIG. 1 is a perspective view of a surgical fastener in accordance with an embodiment of the present disclosure.

Embodiments of the presently disclosed surgical fasteners will now be described in detail with reference to the drawing figures wherein like reference numerals identify similar or identical elements. As used herein and as is traditional, the term "distal" refers to that portion which is farthest from the user while the term "proximal" refers to that portion which is closest to the user.

Figure 2:
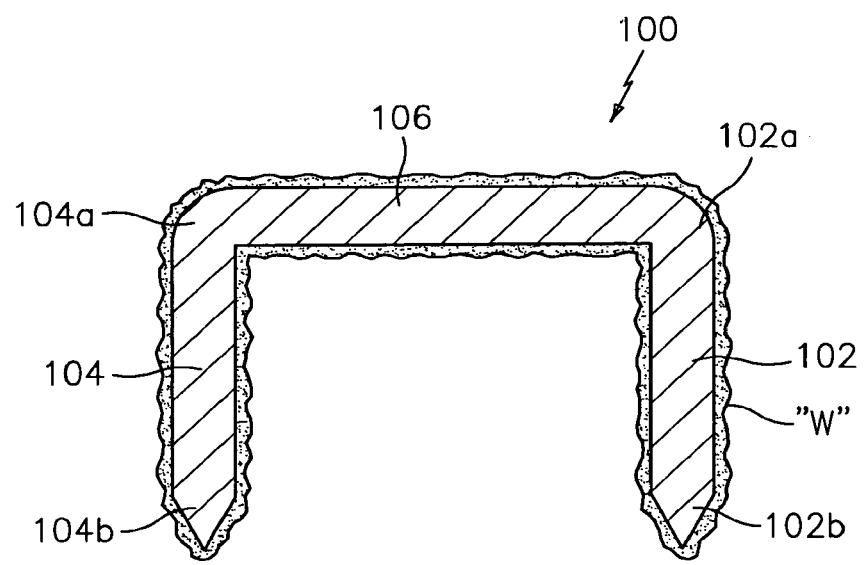
FIG. 2 is a longitudinal cross-sectional view of the surgical fastener of FIG. 1.

With reference to FIGS. 1 and 2, a surgical fastener, in the form of a surgical staple, is generally shown as 100. Surgical staples of the present disclosure typically include any metallic staple used to join together tissue parts and/or adjacent tissues. Surgical staples 100 may be made of metal, such as, for example, stainless steel or titanium, or any other material known by one having skill in the art. For example, surgical staples 100 may also be fabricated from bio-absorbable material or the like.

Bio-absorbable materials used for surgical staples 100 include, and are not limited to, those fabricated from homopolymers, copolymers or blends obtained from one or more monomers selected from the group consisting of gly-colide, glycolic acid, lactide, lactic acid, p-dioxanone, α-caprolactone and trimethylene carbonate. Other bio-absorbable materials include and are not limited to, for example, Polyglycolic Acid (PGA) and Polylactic Acid (PLA).

With continued reference to FIGS. 1 and 2, surgical staple 100 includes a pair of legs 102, 104 which are interconnected to one another by a crown or backspan 106 extending between first ends 102a, 104a, respectively, thereof. As seen in FIGS. 1 and 2, crown 106 is substantially perpendicular to legs 102, 104. However, it is envisioned that crown 106 may take on any shape and/or form as needed and/or desired and may have any orientation relative to legs 102, 104. For example, crown 106 may include two sections which extend angularly from legs 102, 104 and are connected at an apex (not shown).

As seen in FIGS. 1 and 2, respective distal ends 102b, 104b of legs 102, 104 are sharpened to facilitate penetration of legs 102, 104 into tissue or the like.

Figure 3:
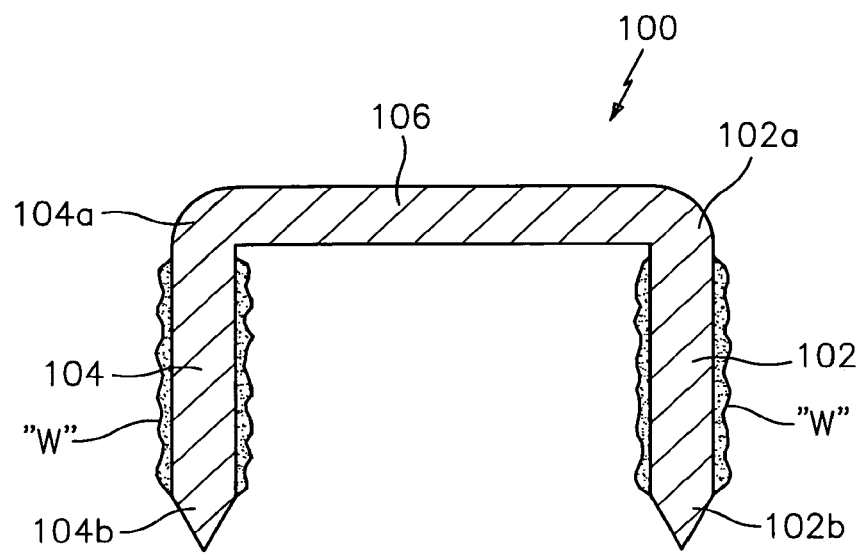
FIG. 3 is a longitudinal cross-sectional view of a surgical fastener according to another embodiment of the present disclosure.
Figure 4:
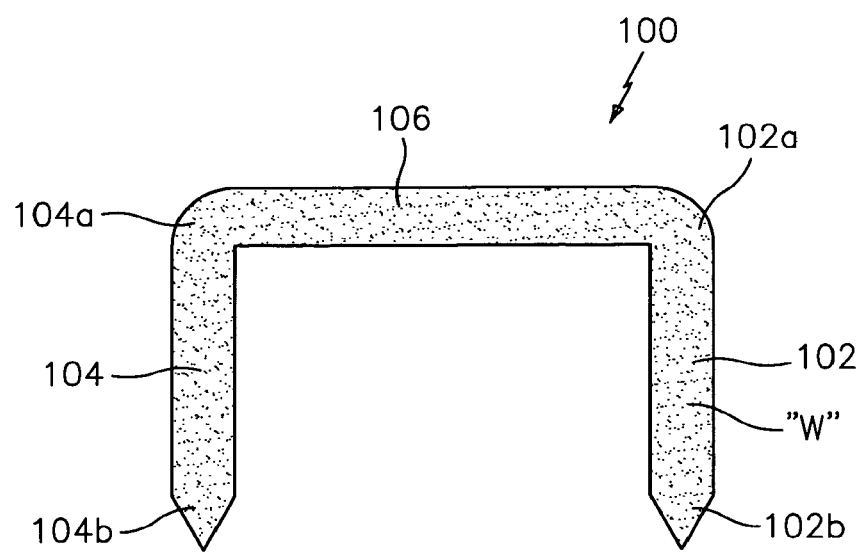
FIG. 4 is a longitudinal cross-sectional view of a surgical fastener according to yet another embodiment of the present disclosure.

In accordance with the present disclosure, surgical staple 100 is coated with a wound treatment material "W". It is envisioned that wound treatment material "W" may be applied to the entirety of surgical staple 100 (as seen in FIGS. 1 and 2), or may be applied to any specific area of surgical staple 100 that is to come into contact with tissue of the like. For example, wound treatment material "W" may be applied solely to legs 102, 104 (see FIG. 3); solely to one of legs 102, 104 (not shown); solely to crown 106 (not shown); or any portion thereof. It is further envisioned that wound treatment material "W" may be impregnated into legs 102, 104 and crown 106 of surgical staple 100, as seen in FIG. 4.

In one embodiment, surgical staples 100 may be fabricated from a bio-absorbable material which is desirably impregnated with wound treatment material "W". Accordingly, in use, the wound treatment material component of surgical staples 100 may function to retard any bleeding which may occur from the tissue, in the manner of a sealant, and to secure the approximated tissue together, in the manner of an adhesive. The bio-absorbability of surgical staples 100 allows for the at least a portion of surgical staples 100 to be absorbed into the body after a predetermined amount of time. For example, surgical staples 100 may remain in place in the body for approximately 2-3 weeks in order for the anastomosis to sufficiently heal prior to surgical staples 100 being absorbed into the body.

As mentioned above and as shown in FIG. 3, it is envisioned that surgical staples 100 may be impregnated with a wound treatment material "W" which is a pre-cured adhesive or sealant. The pre-cured sealant or adhesive will react with the moisture and/or heat of the body tissue to thereby activate the sealing and/or adhesive properties of the sealant or adhesive. It is envisioned that the pre-cured sealant or adhesive may be a hydro-gel or the like.

It is contemplated that the wound treatment material "W" is any material for joining, healing, sealing or otherwise treating tissue. In a preferred embodiment, the wound treatment material is a bio-compatible sealant, including, and not limited to, sealants which cure upon tissue contact, sealants which cure upon exposure to ultraviolet (UV) light, sealants which are two-part systems which are kept isolated from one another and are combined or any combinations thereof. Any known suitable adhesive may be used. In one embodiment, it is contemplated that such sealants and/or adhesives are curable. For example, sealants may have a cure time of from about 10 to 15 seconds may be used. In preferred embodiments, the sealant and/or adhesive is a bioabsorbable and/or bio-resorbable material. In another embodiment, it is contemplated that a sealant and/or adhesive having a cure time of about 30 seconds may be used. It is further envisioned that wound treatment material "W" may be a pre-cured adhesive or sealant.

In certain preferred embodiments, the wound treatment material "W" comprises a sealant. Such a sealant is desirably a PEG-based material. Examples of classes of materials useful as the sealant and/or adhesive include acrylate or methacrylate functional hydrogels in the presence of a biocompatible photoinitiator, alkyl-cyanoacrylates, isocyanate functional macromers with or without amine functional macromers, succinimidyl ester functional macromers with amine or sulfhydryl functional macromers, epoxy functional macromers with amine functional macromers, mixtures of proteins or polypeptides in the presence of aldehyde crosslinkers, Genipin, or water-soluble carbodiimides, anionic polysaccharides in the presence of polyvalent cations, etc.

Some specific materials which may be utilized include isocyanate terminated hydrophilic urethane prepolymers derived from organic polyisocyanates and oxyethylene-based diols or polyols, including those disclosed in U.S. Pat. Nos. 6,702,731 and 6,296,607 and U.S. Published Patent Application No. 2004/0068078; alpha-cyanoacrylate based adhesives including those disclosed in U.S. Pat. No. 6,565,840; alkyl ester based cyanoacrylate adhesives including those disclosed in U.S. Pat. No. 6,620,846; adhesives based on biocompatible cross-linked polymers formed from water soluble precursors having electrophilic and nucleophilic groups capable of reacting and cross-linking in situ, including those disclosed in U.S. Pat. No. 6,566,406; two part adhesive systems including those based upon polyalkylene oxide backbones substituted with one or more isocyanate groups in combination with bioabsorbable diamine compounds, or polyalkylene oxide backbones substituted with one or more amine groups in combination with bioabsorbable diisoycanate compounds as disclosed in U.S. Published Patent Application No. 2003/0032734, the contents of which are incorporated by reference herein; and isocyanate terminated hydrophilic urethane prepolymers derived from aromatic diisocyanates and polyols as disclosed in U.S. Published Patent Application No. 2004/0115229, the contents of which are incorporated by reference herein.

It is envisioned and within the scope of the present disclosure that wound treatment material "W" may include one or a combination of adhesives, hemostats, sealants, or any other tissue or wound-treating material. Surgical biocompatible wound treatment materials "W", which may be used in accordance with the present disclosure, include adhesives whose function is to attach or hold organs, tissues or structures, sealants to prevent fluid leakage, and hemostats to halt or prevent bleeding. Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc. Examples of hemostat materials, which can be employed, include fibrin-based, collagen-based, oxidized regenerated cellulose-based and gelatin-based topical hemostats, as well as aluminum alum (i.e., ammonium alum or aluminum ammonium sulfate). Examples of commercially available hemostat materials are fibrinogen-thrombin combination materials sold under the trade designations CoStasis™ by Tyco Healthcare Group, LP, and Tisseel™ sold by Baxter International, Inc. Hemostats herein include astringents, e.g., aluminum sulfates, and coagulants. A further example of a hemostat includes "Quick Clot™", commercially available from Z-Medica, Inc., Newington, Conn.

The medicament may include one or more medically and/or surgically useful substances such as drugs, enzymes, growth factors, peptides, proteins, dyes, pigments, diagnostic agents or hemostasis agents, monoclonal antibodies, or any other pharmaceutical used in the prevention of stenosis. The medicament may be disposed on structure 100 or impregnated into structure 100.

Wound treatment material "W" may include visco-elastic film forming materials, cross-linking reactive agents, and energy curable adhesives. It is envisioned that wound treatment material "W", and in particular, adhesive may be cured with the application of water and/or glycerin (1, 2, 3,-pranatetriol, also known as glycerol or glycerine) thereto. In this manner, the water and/or glycerin cure the adhesive and hydrate the wound.

It is further contemplated that wound treatment material "W" may include, for example, compositions and/or compounds which accelerate or beneficially modify the healing process when particles of the composition and/or compound are applied to or exposed to a surgical repair site. For example, the wound treatment material "W" may be a therapeutic agent which will be deposited at the repair site. The therapeutic agent can be chosen for its antimicrobial properties, capability for promoting repair or reconstruction and/or new tissue growth. For example, the wound treatment material "W" may comprise "SilvaSorb™", commercially available from AcryMed, Inc, Portland, Oreg. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, wound treatment material "W" may include one or several growth promoting factors, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is further envisioned and within the of the present disclosure for wound treatment material "W" to include any microbial agent, analgesic, growth factor, and anti-inflammatory agent known by one having skill in the art or any combination thereof.

Those skilled in the art will recognize that the successful surface treatment of surgical staple 100, prior to the application of wound treatment material "W", may include pre-cleaning surgical staple 100 and controlling the moisture at the surface of surgical staple 100 in order to ensure complete and/or proper coating of surgical staple 100. Multi-step cleaning and drying operations can therefore be used to provide a clean surface and to control moisture. Once the surface of surgical staple 100 is treated, as described above, a solution containing wound treatment material "W" is applied to the treated surgical staple 100.

It is contemplated and within the scope of the present disclosure for any of the surgical staples 100 disclosed herein to be used in connection with linear-type surgical staplers, non-linear-type surgical stapler, annular-type surgical staples, endoscopic-type surgical staplers, skin-type surgical staplers and the like.

It is further contemplated and within the scope of the present disclosure for any of the surgical staples 100 disclosed herein to have equal length legs, un-equal length legs, a relatively short crown as compared to the length of the legs, a relatively long crown as compared to the length of the legs, a symmetrical transverse cross-sectional profile in at least one of the legs and the crown, and an asymmetrical transverse cross-sectional profile in at least one of the legs and the crown. For example, each leg and/or the crown may have a cross-sectional profile which is polygonal, such as, triangular, rectangular, hexagonal any combination thereof or the like. Moreover, each leg and/or the crown may have a cross-sectional profile which is circular, ovular or the like. It is further envisioned that the crown may be either linear of non-linear.

It is still further contemplated and within the scope of the present disclosure for any of the surgical staples 100 disclosed herein to include legs which do not lie in the same plane as one another. In other words, one leg and the crown of the surgical staple 100 define a first plane, and the other leg of the surgical staple 100 lies in a second plane which is non-coplanar, or transverse to the first plane.

Figure 5:
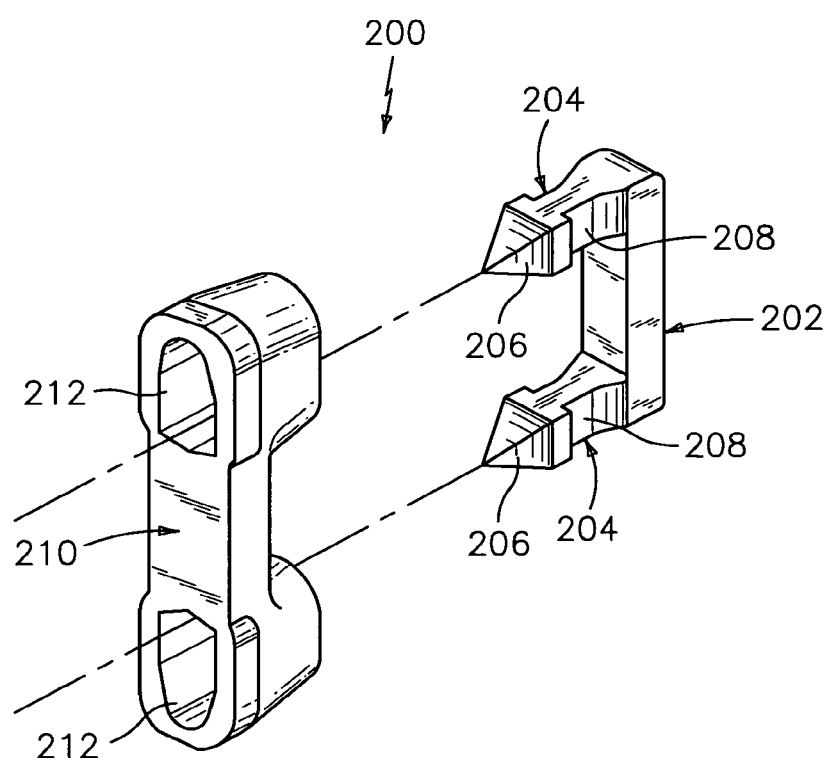
FIG. 5 is a perspective view of an exemplary two-part fastener constructed in accordance with the present disclosure.

As seen in FIG. 5, a surgical fastener, in the form of a two-part fastener, is generally shown as 200. The physical structure of an exemplary surgical fastener 200 is shown and described in U.S. Pat. No. 4,534,352, the entire content of which is incorporated herein by reference. Generally, surgical fastener 200 includes a retainer member 210 and fastener member 202, which has two prongs or legs 204 that are driven through tissue (not shown) to engage apertures 212 in retainer member 210. Prongs 204 each include a barb 206 attached to a shank 208.

In accordance with the present disclosure, surgical fastener 200, including retainer member 210 and fastener member 202 may be constructed from any of the materials disclosed hereinabove either identically (constructed from the same materials) or uniquely (i.e., constructed from different materials) from one another.

It should be understood that various changes in form, detail and application of the support structures of the present disclosure may be made without departing from the spirit and scope of the present disclosure.

What is claimed is:

1. A surgical fastener for use in combination with a surgical fastener applying apparatus, the surgical fastener comprising:
 a pair of legs;
 a crown interconnecting the pair of legs; and
 a wound treatment material impregnated into the legs and the crown, the fastener being made of at least one of stainless steel and titanium, and the wound treatment material includes a material selected from the group consisting of glycolide, glycolic acid, lactide, lactic acid, p-dioxanone, α-caprolactone and trimethylene carbonate.

2. The surgical fastener according to claim 1, wherein the surgical fastener is a staple.

3. The surgical fastener according to claim 1, wherein the surgical fastener comprises a two-part fastener.

4. The surgical fastener according to claim 1, wherein the material is at least one of Polyglycolic Acid (PGA) and Polylactic Acid (PLA).

5. The surgical fastener according to claim 1, further comprising hemostat selected from the group consisting of fibrin-based, collagen-based, oxidized regenerated cellulose-based and gelatin-based topical hemostats.

6. The surgical fastener according to claim 1, further comprising a medicament selected from the group consisting of drugs, enzymes, growth factors, peptides, proteins, dyes, diagnostic, agents or hemostasis agents, monoclonal antibodies, or any other pharmaceutical used in the prevention of stenosis.

7. The surgical fastener according to claim 1, wherein each leg includes a sharpened distal end.

8. The surgical fastener according to claim 1, wherein the crown is linear.

\* \* \* \* \*